United States Patent [19]
Kizelshteyn et al.

[11] Patent Number: 5,215,105
[45] Date of Patent: Jun. 1, 1993

[54] METHOD OF TREATING EPIDURAL LESIONS

[75] Inventors: Grigory Kizelshteyn, Bronx, N.Y.; James E. Heavner, Lubbock, Tex.; Edward I. McNamara, Chelmsford; Kenneth J. Daignault, Jr., Jefferson, both of Mass.

[73] Assignee: Custom Medical Concepts, Inc., Chelmsford, Mass.

[21] Appl. No.: 436,316

[22] Filed: Nov. 14, 1989

[51] Int. Cl.$^5$ .............................. A61B 17/00
[52] U.S. Cl. ........................ 128/898; 604/164
[58] Field of Search .......... 606/192, 194; 128/898; 604/164, 96, 264, 281

[56] References Cited

U.S. PATENT DOCUMENTS

| | | | |
|---|---|---|---|
| 3,635,223 | 1/1972 | Klieman | 606/194 |
| 3,856,009 | 12/1974 | Winnie | 604/164 |
| 4,162,673 | 7/1979 | Patel | 128/748 |
| 4,284,084 | 8/1981 | Binard et al. | 128/748 |
| 4,299,226 | 11/1981 | Banka | 606/194 X |
| 4,518,383 | 5/1985 | Evans | 604/164 X |
| 4,519,403 | 5/1985 | Dickhudt | 128/785 |
| 4,581,017 | 4/1986 | Sahota | 606/192 X |
| 4,588,398 | 5/1986 | Daugherty et al. | 604/164 X |
| 4,801,293 | 1/1989 | Jackson | 604/51 |

*Primary Examiner*—Michael H. Thaler
*Attorney, Agent, or Firm*—Wolf, Greenfield & Sacks

[57] ABSTRACT

A method for treating fibrotic lesions in the epidural space of the spinal column includes the steps of percutaneously inserting into the epidural space and across a fibrous lesion, a catheter carrying a compliant, inflatable balloon which is expandable both radially and longitudinally, and, expanding the balloon radially so as to contact the walls of the epidural space and disrupt the fibers of the lesion, and thereafter expanding the balloon longitudinally within the epidural space so as to increase the area of contact between the balloon and the walls of the epidural space. An introducer for percutaneously inserting a catheter or other medical device into the epidural space includes a polymeric tubular shaft having a tapered, curved distal tip through which the catheter is advanced and retracted.

14 Claims, 7 Drawing Sheets

METHOD OF TREATING EPIDURAL LESIONS

FIELD OF THE INVENTION

This invention relates to a method for treating fibrotic lesions in the epidural space of the spinal column, and to a catheter system to facilitate such a method and to an improved catheter introducer for accessing the epidural space.

BACKGROUND OF THE INVENTION

In the human body, the epidural space is a narrow channel, located in and extending the length of the spine. FIGS. 1A and 1B illustrate, diagrammatically, the generally crescent shape cross-section of the epidural space 10 and its position within the spinal column 8. The epidural space 10 is defined along one edge or side by the dura mater 12 which surrounds the spinal cord 18. The epidural space is further defined along a second edge or side by the periosteum of the bony vertabrae or by the ligamentum-flavum 14 at the vertabral interspaces. Along the interior surface of the periosteum of the bony vertebrae or of the ligamentum-flavum 14 lies the venus plexis 19, a complex configuration of veins. Web-like fibrosis 20 may adhere to the dura mater 12 and the periosteum of the bony vertebrae and/or the ligamentum-flavum 14 in a random manner or in layers which form lesions extending across the epidural space 10 or parallel thereto. The fibrosis comprising an epidural lesion may have a consistency ranging from very soft to tougher, scar-tissue. An epidural lesion may extend through the epidural space over the length of two or three vertebrae. Such lesions are believed to be a source of lower back pain and possibly sciatica in human beings. These lesions are believed to be caused primarily by post operative scarring of nerves, particularly from laminectomy procedures. A ruptured disc or a leaking disc, caused by an annular tear, also are believed to be causes of epidural lesions.

Epidural lesions may be treated by surgical exploration. Unfortunately, such surgical exploration is difficult, time-consuming and often results in a painful post-operative recovery. Epidural lesions also have been removed by a method known as fluid lysis. In fluid lysis, an epidural catheter, typically comprising a flexible tubular shaft having an open distal end, is introduced between the vertebrae of the spinal column into the epidural space. The distal end of the epidural catheter is positioned adjacent the fibrosis comprising the lesion. A large volume of fluid is delivered through the catheter and directed against the fibrosis with enough force to break the web-like layers comprising the lesion. Unfortunately, fluid lysis may be ineffective because the fluid takes the path of least resistance upon leaving the distal end of the catheter, and often fails to impact the fibrosis with enough force to destroy the lesion. Consequently the lesion may not be completely removed and the procedure must be repeated.

Therefore it is among the general objects of the present invention to provide an improved method of treating fibrous lesions in the epidural space which avoids the foregoing and other difficulties.

In procedures, such as fluid lysis, which require introducing a catheter into the epidural space, it has long been standard practice to use a hollow metal needle having a knife-like distal tip, such as a Touhy or Huber needle, to penetrate the tough fibrous tissues surrounding the epidural space. The columnar strength and collapse resistance of the metal needle overcomes the resistance of the ligamentum-flavum and assists in maintaining the angle and position of the needle in the epidural space while the catheter is introduced into the epidural space through the needle. Although proper positioning of a catheter in the epidural space often requires advancing and retracting the catheter through the distal tip of the needle introducer. Unfortunately, the knife-like distal tip of the needle introducer is likely to damage and even shear off the catheter as the catheter is retracted possibly resulting in a severed portion of the catheter remaining in the epidural space. Difficult, complex surgery is necessary to retrieve such a severed portion from the epidural space. To avoid such a result, anesthesiologists traditionally have been taught never to withdraw or pull back a catheter through the metal needle introducer. Traditionally, positioning occurs by withdrawal of the catheter and the introducer needle simultaneously, with the positions of the two relative to one another remaining unchanged. Such a technique often results in multiple punctures before the catheter is positioned as desired in the epidural space.

More recently, in order to enable retraction of the epidural catheter, catheters having metal spring-like wire coverings have been introduced into the epidural space using Huber-type needles, in which the needle lumen opens at an angle with respect to the axis of the needle. The metal spring-like covering is less likely to be severed and may allow for limited reciprocating motion of the catheter through the needle introducer during positioning of the catheter. Although the risk of shearing such a spring reinforced catheter is not as high as with a conventional catheter, the risk of damaging the catheter still is very high.

The use of metal needle introducers has further discouraged the insertion into the epidural space of other medical devices, such as flexible fiberscopes and microsurgical instruments, because of the same risks associated with catheters.

Therefore it also is among the general objects of the invention to provide a catheter introducer for placing a catheter or other medical devices in the epidural space which avoids the foregoing and other difficulties.

SUMMARY OF THE INVENTION

In accordance with the invention, an improved method of treating fibrotic lesions in the epidural space of the spinal column involves percutaneously inserting, into the epidural space and across an epidural lesion, a catheter carrying a dilatation balloon which is expandable both radially and longitudinally. The catheter is manipulated to locate the balloon within the lesion and the balloon then is expanded radially toward the walls of the epidural space. The expanding balloon exerts pressure on the lesion thereby severing and compressing the fibers that compose the lesion. Thereafter, while maintaining radially outward pressure against the walls of the epidural space, the balloon is expanded longitudinally so as to increase the area of the balloon surface in contact with the lesion and further disrupt its fibers.

In accordance with another aspect of the invention, a new catheter introducer is provided for introducing catheters or other medical devices into the epidural space of the spinal column. The introducer is formed from a relatively soft, flexible material, such as an appropriate plastic and includes a tubular shaft extending along a central axis, the shaft having proximal and distal ends and a central lumen extending therethrough. The distal end of the shaft has a memory-shaped curve which deviates from the central axis of the shaft. The curve enables the distal outlet of the introducer to be more closely oriented to the longitudinal axis of the epidural space or to provide initial direction to the catheter toward a specific area of the epidural space. The shaft is formed from a semi-soft polymer which, preferably, has radiopaque characteristics. The proximal end of the tubular shaft is coupled to a proximal luer fitting.

Another aspect of the invention relates to a method for introducing a catheter into the epidural space of the spinal column and includes the steps of mounting the above-described catheter introducer on a needle or trocar and percutaneously inserting the catheter introducer and the needle into the epidural space of the spinal column. The needle or trocar then is withdrawn from the catheter introducer, and the distal end of the catheter introducer assumes its curved memory shape. A catheter is then advanced through the central lumen of the catheter introducer and into the epidural space. The introducer is free of hard, sharp edges. The catheter may be positioned by advancing and retracting the catheter, through the introducer, as desired. After the catheterization procedure is completed, the catheter is withdrawn through the lumen of the catheter introducer. The catheter introducer is thereafter withdrawn from the epidural space.

It is among the general objects of the invention to provide an improved method for treating fibrous lesions in the epidural space which avoids the disadvantages of prior art methods.

Another object of the present invention is to provide a method of treating fibrous lesions in the epidural space in which a balloon catheter is percutaneously inserted into the fibrosis comprising an epidural lesion and inflated to disrupt and rupture the fibrosis.

A further object of the present invention is to provide a method for treating a fibrous lesion in the epidural space in which the balloon of a dilatation catheter first is expanded radially to exert outward pressure on the lesion and thereafter is expanded longitudinally within the lesion while maintaining the pressure against the walls of the epidural space.

A further object of the present invention is to provide a catheter system for percutaneously performing medical procedures in the epidural space.

Still a further object of the present invention is to provide a percutaneous introducer for accessing the epidural space through which a catheter may be withdrawn from the epidural space without damaging the catheter.

Yet another object of the present invention is to provide a catheter introducer for introducing catheters or other medical devices into the epidural space in which the introducer is made of a sheath of semi-rigid polymer having good columnar strength and collapse resistivity.

A further object of the present invention is to provide a catheter introducer for introducing catheters into the epidural space in which the distal end of the catheter introducer has a shape memory which, after percutaneous insertion into the epidural space, imparts a curve to the distal tip of the catheter introducer to direct the catheter longitudinally along the epidural space.

Yet another object of the present invention is to provide such a catheter introducer that is made of a radiopaque material to facilitate fluoroscopic monitoring of its position within the epidural space.

Yet another object of the present invention is to provide a catheter introducer which may be left indwelling in the epidural space with reduced risk to the patient than with conventional metal introducers.

Yet another object of the present invention is to provide a method for percutaneously placing a catheter in the epidural space in which a semi-rigid sheath is inserted percutaneously into the epidural space and the catheter is inserted through the sheath and in which the catheter may be advanced and retracted relative to the sheath during positioning.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

In accordance with the invention, a method for treating fibrotic lesions in the epidural space of the spinal column involves percutaneously inserting a balloon catheter into the epidural space of the patient and, with the balloon positioned across the fibrotic lesion, inflating the balloon both radially and longitudinally to sever or disrupt the fibrosis comprising the epidural lesion. Referring to FIGS. 2-5, a catheter system suitable for use with the present invention comprises a catheter introducer 24, a guidewire 32 and a balloon dilatation catheter 30.

Figure 1A:
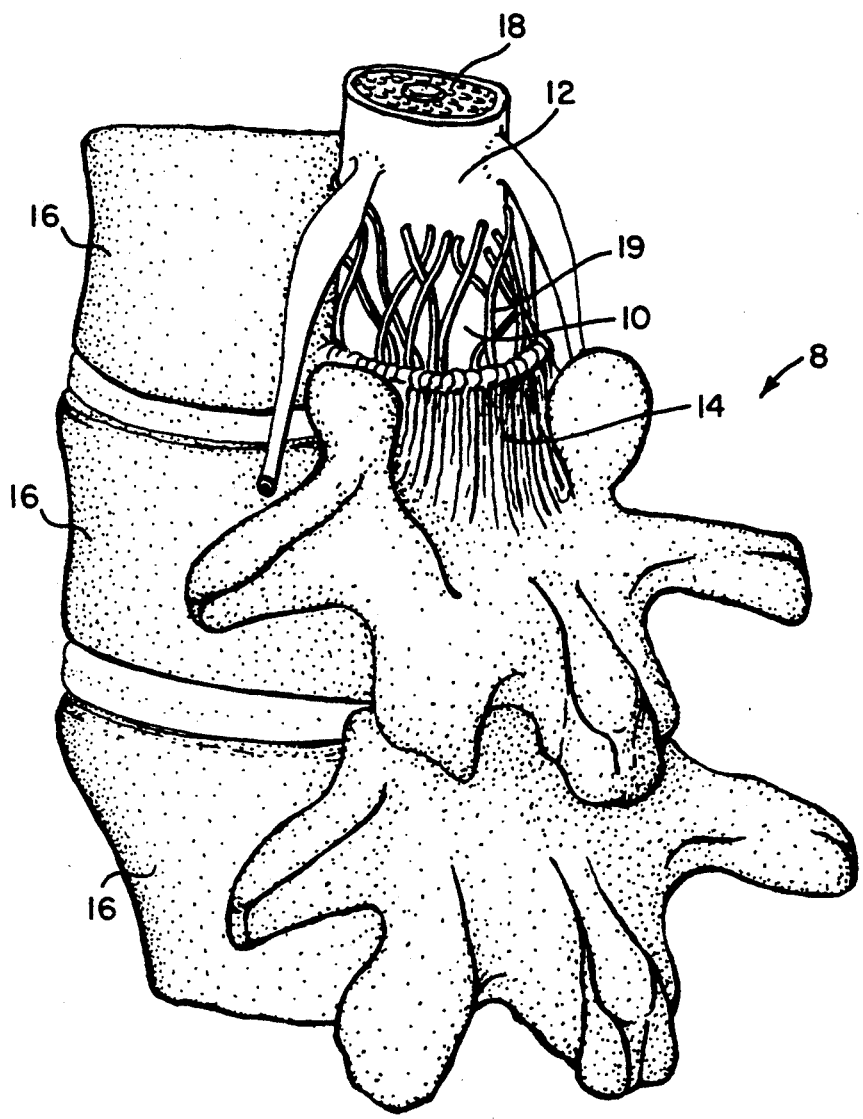
FIG. 1A is a fragmented perspective view of a section of the human spinal column illustrating the position of the epidural space.
Figure 1B:
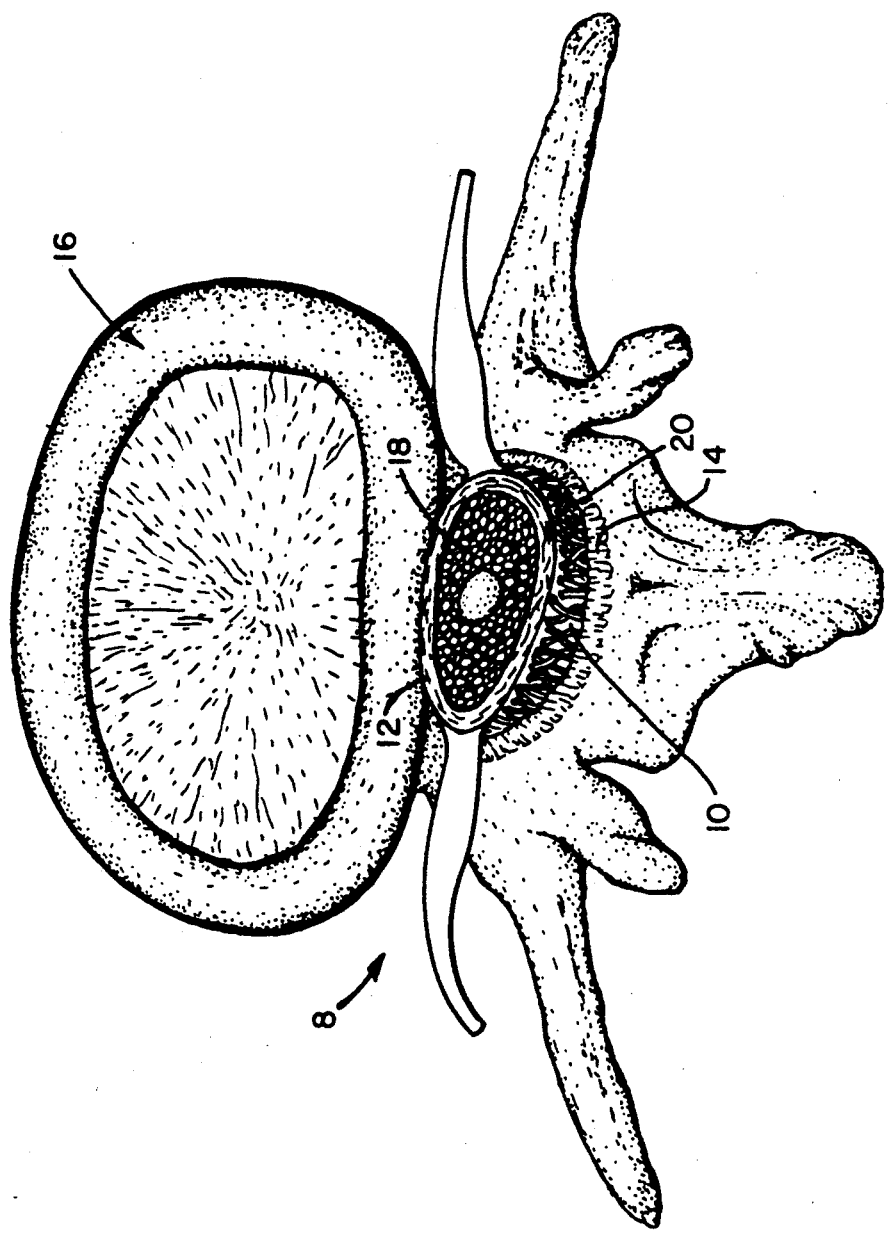
FIG. 1B is a cross-sectional view seen transversely to the axis of the human spinal column further illustrating the position and shape of the epidural space and the fibers comprising an epidural lesion.
Figure 2:
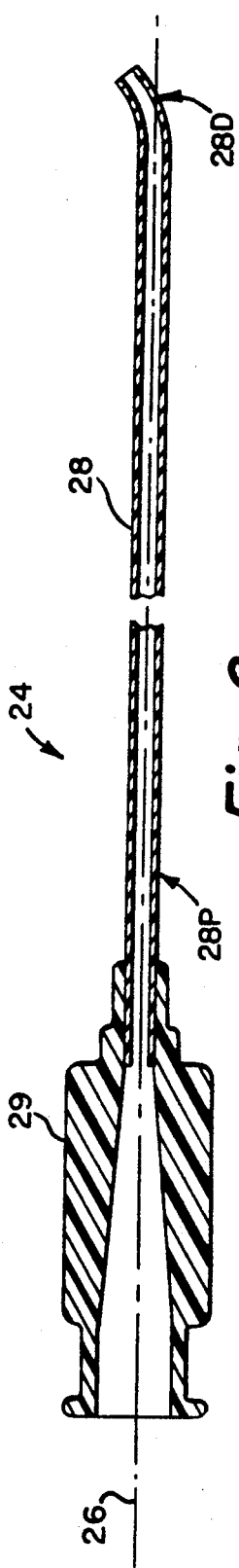
FIG. 2 is an enlarged longitudinal sectional illustration of a catheter introducer of the present invention.

FIG. 2 illustrates, diagrammatically, the cross-sectional configuration of catheter introducer 24. Catheter introducer 24 is comprised of a tubular shaft 28 which extends about a central axis 26. The distal tip 28D of shaft 28 is curved as indicated. In the preferred embodiment, shaft 28 may be formed from a semi-soft polymer which provides good columnar strength and collapse resistivity while allowing some flexibility. A polymer suitable for forming shaft 28 is a polyester elastomer available from DuPont under the trade name of Hytrel, type 7246 72D. In the preferred embodiment, shaft 28 is radiopaque to facilitate fluoroscopic monitoring of its position while in the epidural space. A Hytrel compound which has been doped with 25% bismuth, to add radiopacity, is available in extruded form from Medical Profiles Incorporated, The most distal 10 millimeters of shaft 28 is heat formed into a distal tip 28D having a memory-shape curve or deviation from axis 26 of approximately 20° to 30°. Proximal end 28P of catheter introducer 24 is connected to a proximal luer fitting 29. Shaft 28 may be approximately 66 mm end to end or longer, and has an outer diameter of approximately 0.077 inches and an inner diameter of approximately 0.061 inches. The most distal 4 to 5 millimeters of distal tip 28D are formed on a mandrel to taper slightly to an inner diameter of approximately 0.059 inches to fit tightly about a 17 gauge needle. In addition to the tapering of the inner diameter, the most distal millimeter of shaft 28 has a tapered outer diameter to create a tapered tip to avoid damaging a catheter shaft as it is withdrawn through catheter introducer 24 and to facilitate penetration of tissues during insertion into the epidural space.

The guidewire 32 of the catheter system may be of the small diameter, steerable type commonly used in coronary angioplasty, as disclosed, for example, in U.S. Pat. No. 4,545,390, to Leary. The guidewire has a radiopaque distal portion to enable the movement of its distal end to be observed fluoroscopically.

Figure 3:
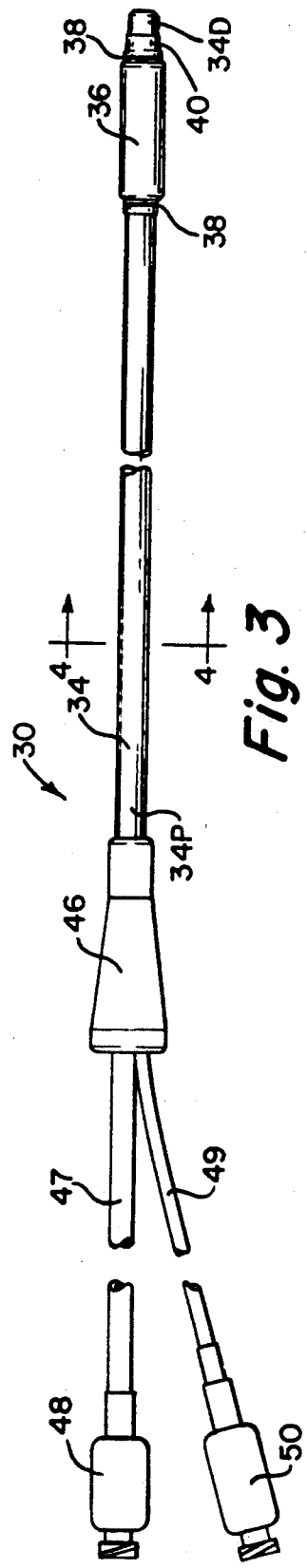
FIG. 3 is a fragmented illustration of a balloon dilatation catheter for use in the method of the present invention.
Figure 4:
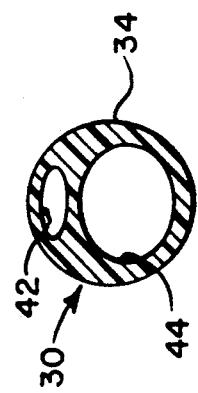
FIG. 4 is a cross sectional illustration of the balloon dilation catheter of FIG. 3 as seen along lines 4—4 of FIG. 3.

The balloon dilatation catheter 30 is illustrated, diagrammatically, in FIGS. 3 and 4 and is comprised of an elongate flexible shaft 34, extruded from polyethylene or other suitable polymer. Shaft 34 has an inflation lumen 42 and a guidewire lumen 44 extending therethrough. Inflation lumen 42 communicates, at its distal end, with the interior of the balloon. Guidewire lumen 44 remains open at the distal end of shaft 34. The distal end of inflation lumen 42 is blocked, distally of the balloon. The proximal end 34P of shaft 34 is attached to Y-connector 46 which bifurcates the lumens into a guidewire tube 47 and balloon tube 49, which are connected to proximal luers 48 and 50, respectively. In the preferred embodiment, shaft 34 may be approximately 58 cm in length from the Y-connector 46 to its distal end, and about 73 cm in length overall. Shaft 34 may have an outer diameter of about 0.038 inches. Guidewire lumen 44 may have a diameter of about 0.018 inches and inflation lumen 42 may have a cross sectional dimension of approximately 0.01 inches.

A dilatation balloon 36 is mounted on the distal end of shaft 34. Balloon 36, in the preferred embodiment, may be formed from a sleeve of compliant material, such as latex or silicone rubber. The latex sleeve used to make balloon 36 is preferably at least 0.039 inches long. The distal end of balloon 36 is tied to catheter shaft 34 by wound thread 38, preferably Dacron thread. In the manufacture of the catheter, the balloon 36 is stretched approximately 70% above its relaxed length to assure that, when collapsed, it will fit closely about shaft 34. The proximal end of balloon 36 is then similarly tied to shaft 34 by a thread winding 38. The proximal and distal ends of balloon 36 and the thread windings 38 then may be covered with a bonding agent to protect the proximal and distal windings from damage. Because of its stretched configuration, upon inflation, balloon 36 expands concentrically about shaft 34. The balloon, when mounted, is about 15 mm long, and the length from the distal end of balloon 36 to the distal tip 34D of shaft 34 being approximately 7 mm.

Balloon 36 is preferably a low pressure, high-volume balloon. The inflated outer diameter of the balloon is dependent upon the space in which the balloon is inflated. Once the balloon reaches a maximum radial dilation, it expands longitudinally within the epidural space. In this manner, the expansion of the balloon is adequate to rupture the fibrosis of the epidural lesion while preventing damage within the nerves within the epidural space or damage to the dura mater and the spinal column itself. The maximum pressure at which the balloon may be inflated is about 250 mm Hg. Balloon inflation time preferably should not exceed 10 seconds, while balloon deflation time should not exceed 30 seconds. The volume of balloon 36 when inflated is preferably less than 1 cc. The balloon may be inflated and deflated by a suitable liquid. The syringe is a conventional syringe (not shown) connected to balloon luer.

Figure 5A:
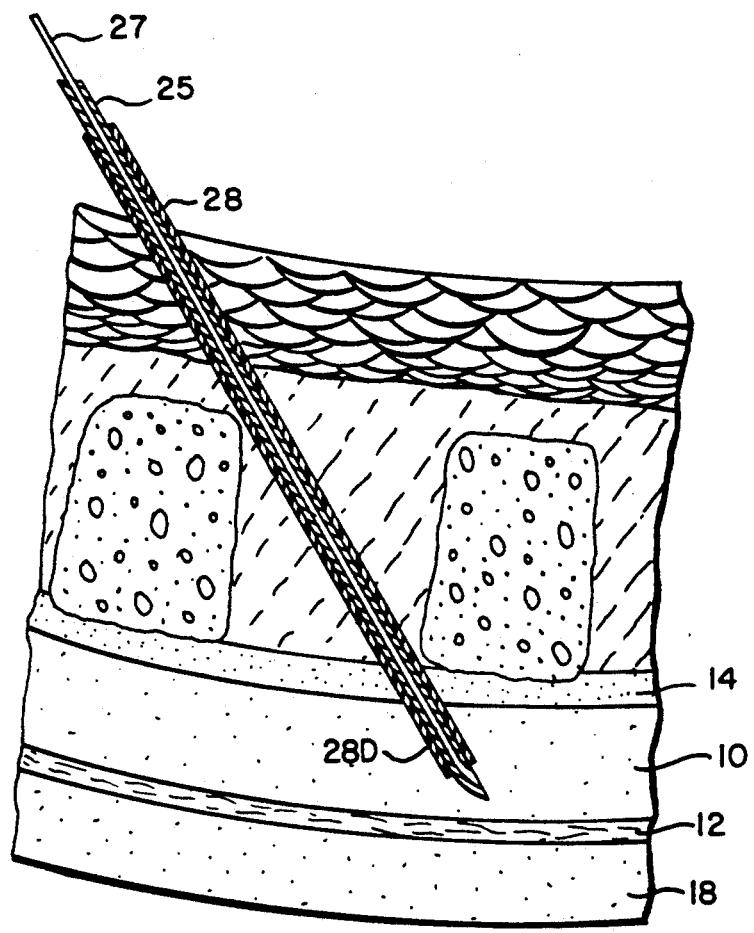
FIG. 5A is a somewhat diagrammatic sectional illustration of the distal end of the catheter introducer of FIG. 2 mounted on a straight needle, illustrating the angle at which the catheter introducer enters the epidural space.
Figure 5B:
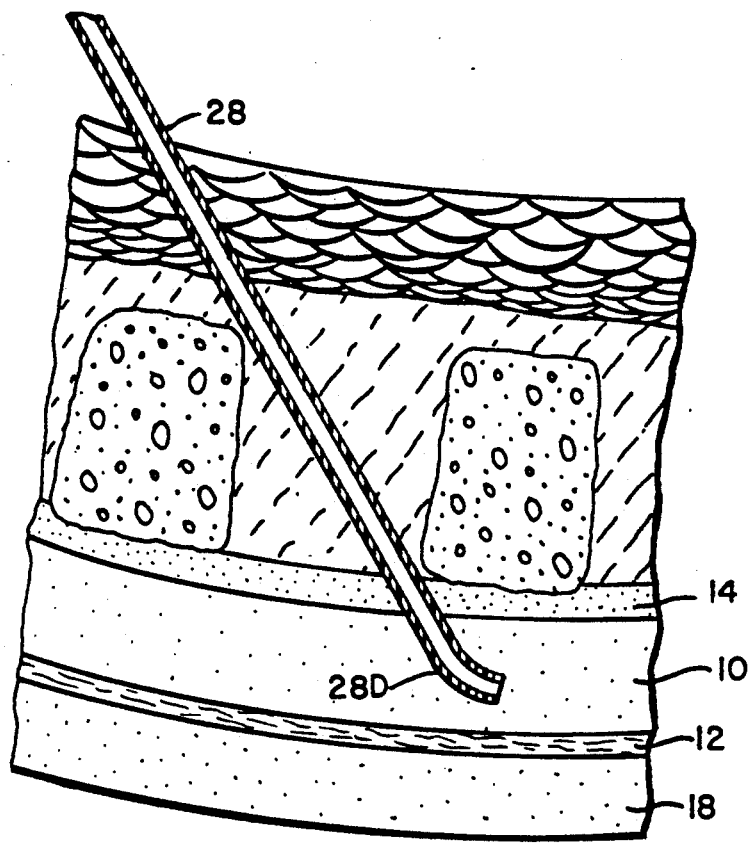
FIG. 5B is a diagrammatic illustration of the distal end of the catheter introducer of FIG. 5A further showing the curved shape assumed by the introducer upon withdrawal of the needle.

According to the present invention, a method for treating fibrous lesions in the epidural space of the spinal column utilizes a catheter system as described above. A marker band 40, preferably made of a radiopaque material, is positioned just distally of balloon 36, to facilitate fluoroscopically monitoring the position of the catheter. The lesion site may be located with dye or other contrast agents injected into the epidural space. The catheter introducer 24 is mounted on a 17 gauge hollow metal needle 25 which has stylet 27 coaxially disposed therein to prevent coring and to straighten the curved distal tip 28D of shaft 28. The catheter introducer 24 and needle are inserted percutaneously to penetrate the ligamentum-flavum 14 at an acute angle as indicated in FIG. 5A. Upon withdrawal of the stylet 27 and needle 25 from the lumen of catheter introducer 24, distal tip 28D of shaft 28 assumes its preformed curved shape which is then oriented toward the longitudinal axis of the epidural space, as indicated in FIG. 5B.

Figure 5C:
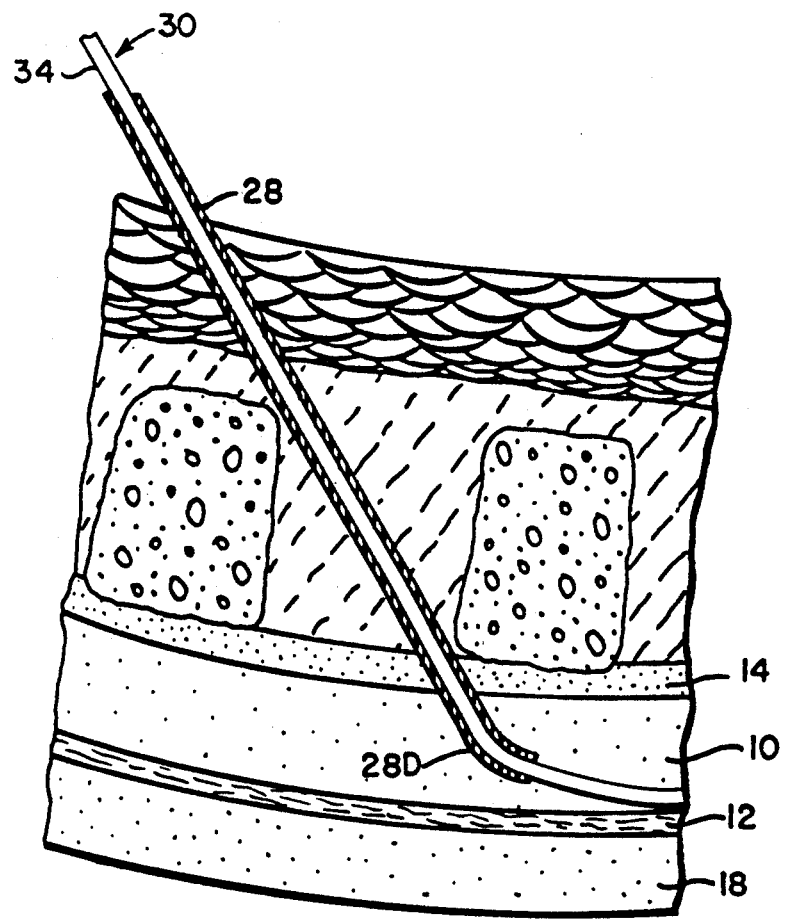
FIG. 5C is a diagrammatic illustration of the distal end of the catheter introducer of FIG. 5B further illustrating the orientation of the catheter with respect to the axis of the epidural space.
Figure 6A:
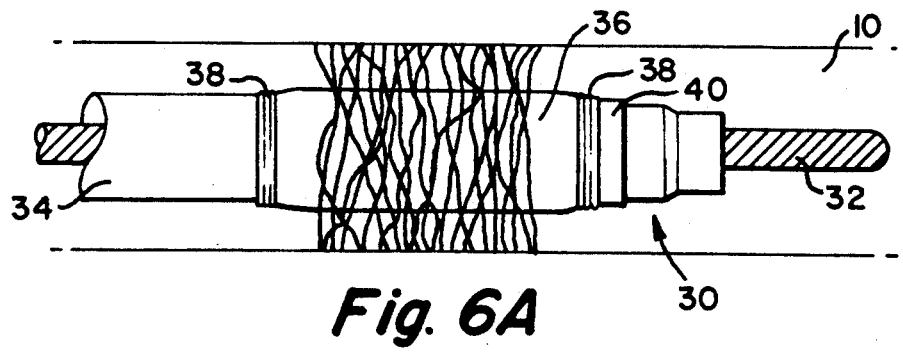
FIG. 6A is a sectional illustration of the balloon end of the catheter of FIG. 3 located in a lesion in the epidural space in accordance with the method of the present invention.

Typically, once catheter introducer 24 is positioned, guidewire 32 is received within guidewire lumen 44 of catheter 30 and the catheter and guidewire advanced through the catheter introducer 24 and into epidural space 10. The curvature of distal tip 28D orients guidewire 32 and catheter 30 substantially parallel with the axis of the epidural space 10, or in a direction toward a specific area of the epidural space, as indicated in FIG. 5C. Guidewire 32 is then advanced to the site of the epidural lesion, its position being fluoroscopically monitored during advancement within the epidural space. Depending on the density of the fibrosis comprising an epidural lesion, guidewire 32 may have to rupture some of the fibrosis to allow penetration of the lesion. Catheter 30 is further advanced over guidewire 32 and positioned across the lesion, as shown in FIG. 6A. In positioning catheter 30, the catheter may be advanced and retracted through the lumen of shaft 28 of catheter introducer 24 without damaging catheter shaft 34 of catheter 30. Positioning of balloon 36 at the lesion site is facilitated by marker band 40 which allows fluoroscopic monitoring of the catheter 30. Alternatively, guidewire 32 may be preloaded into guidewire lumen 44 of catheter 30 and the guidewire and catheter advanced simultaneously through the epidural space and into the lesion, their positions being fluoroscopically monitored during advancement.

Figure 6B:
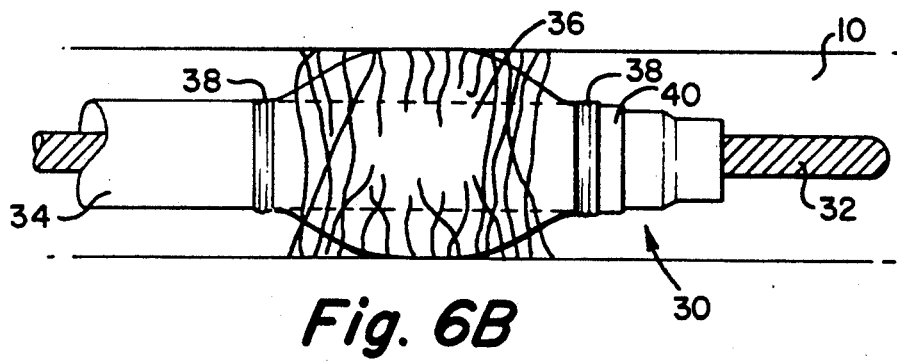
FIG. 6B is an illustration of the balloon end of the catheter of FIG. 6A further illustrating the radial expansion of the balloon against the walls of the epidural space and the rupturing of the fibrous lesion.
Figure 6C:
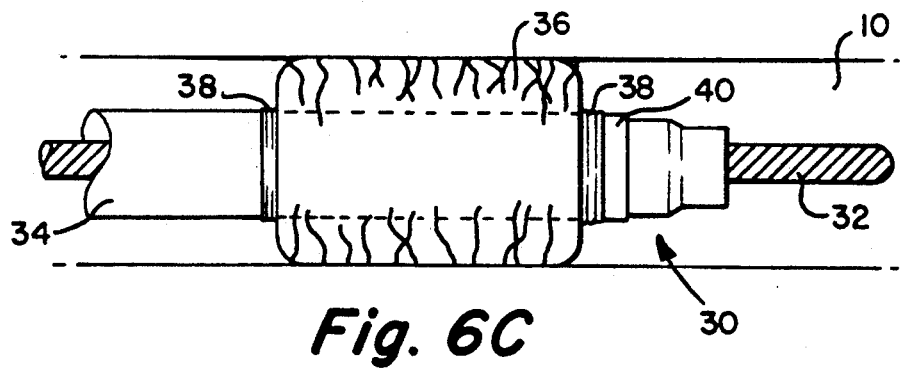
FIG. 6C is a diagrammatic illustration of the balloon end of the catheter of FIG. 6B further illustrating the longitudinal expansion of the balloon within the epidural space.

Once catheter 30 is in position, a syringe is used to deliver liquid, under pressure, via inflation lumen 42, to inflate balloon 36. As balloon 36 inflates, it expands radially outwardly, concentrically about shaft 34, rupturing and dislodging the fibrosis as it expands. As inflation of balloon 36 continues, the outer diameter of the balloon expands toward the walls of the epidural space compressing the fibrosis therebetween, exerting a force against the walls of the epidural space, as shown in FIG. 6B. As inflation continues further, the pressurized fluid in the balloon interior finds the path of least resistance, causing the balloon to expand longitudinally within the epidural space and parallel to the axis of shaft 34. As balloon 36 expands longitudinally, the force against the walls of the epidural space is maintained. In this manner, the longitudinal expansion of balloon 36 further increases the surface area of the balloon which contacts, ruptures and compresses the fibrosis of the lesion, as shown in FIG. 6C.

The size and shape of the epidural space will affect the extent of radial and longitudinal expansion of balloon 36. An epidural space having a narrow cross-sectional profile will cause balloon 36 to have decreased radial expansion while having increased longitudinal expansion within the epidural space. Conversely, an epidural space having a wider cross-sectional profile will cause increased radial expansion and only minimal longitudinal expansion of balloon 36. It may be appreciated that the bidirectional expansion of balloon 36, brought about by the cooperation of the balloon with the walls of the epidural space, facilitates the dilation of a significant area of the epidural space causing the severing and compression of the fibrosis which comprise an epidural lesion. After balloon 36 has been inflated and the fibrosis treated, the syringe assembly applies negative pressure to the interior of the balloon causing deflation of the balloon. The catheter 30 then may be repositioned to treat an adjacent portion of the same lesion or to treat another lesion at a different site. After the dilatation(s) have been completed, catheter 30 is withdrawn from the epidural space through catheter introducer 24. The Dacron thread windings 38 which bind balloon 36 to shaft 34 prevent the balloon from being damaged as it is withdrawn through shaft 28 of catheter introducer 24.

Following withdrawal of catheter 30 through catheter introducer 24, the catheter introducer may be withdrawn from the epidural space. Alternately, a non-balloon catheter, suitable for long term placement in the epidural space, may be inserted through catheter introducer 24 and the introducer thereafter removed from the epidural space.

It may be appreciated that the above-described method may be used to insert other medical devices, such as flexible fiberscopes and microsurgical instruments, into the epidural space through catheter introducer 24, as will be apparent to those skilled in the art.

From the foregoing, it will be appreciated that the invention provides an improved method of treating epidural lesions and a spinal epidural catheter for performing such method as well as providing a new introducer for use in the epidural space. It should be understood, however, that the foregoing description of the invention is intended merely to be illustrative thereof and that other modifications, embodiments and equivalents may be apparent to those skilled in the art without departing from its spirit.

Having thus described in the invention what is claimed is:

1. A method for positioning medical devices in the epidural space of the spinal column comprising the steps of:

providing an introducer comprising a semi-rigid, tubular shaft having a central lumen extending therethrough, the shaft having a memory-shaped, curved distal end and a proximal end connected to a fitting;

inserting a straight needle into the central lumen of the introducer shaft and distally therebeyond;

percutaneously inserting the introducer and the needle into the epidural space of the spinal column;

withdrawing the needle -from the central lumen of the introducer shaft, whereby the distal end of the introducer assumes its curved, memory shape; and advancing a medical device through the central lumen of the introducer shaft and into the epidural space.

2. A method as defined in claim 1 further comprising the step of:

positioning the medical device in the epidural space by advancing and retracting the medical device with respect to the distal end of the introducer.

3. A method as defined in claim 2 further comprising the step of:

withdrawing the medical device through the lumen of the introducer shaft.

4. A method as defined in claim 3 further comprising the step of:

withdrawing the introducer from the epidural space of the spinal column.

5. A method as defined in claim 2 in which the medical device comprises a catheter.

6. A method as defined in claim 2 in which the medical device comprises a flexible fiberscope.

7. A method as defined in claim 2 in which the medical device comprises a microsurgical instrument.

8. A method as defined in claim 2 in which the medical device comprises a guidewire.

9. A method as defined in claim 1 further comprising the step of:

visually monitoring the position of the introducer within the epidural space of the spinal column.

10. A method as defined in claim 9 in which the step of visually monitoring the position of the introducer comprises fluoroscopically monitoring the position of the introducer.

11. A method as defined in claim 1 further comprising the step of:

visually monitoring the position of the medical device within the epidural space of the spinal column.

12. A method as defined in claim 11 in which the step of visually monitoring the position of the medical device comprises fluoroscopically monitoring the position of the medical device.

13. A method as defined in claim 1 in which the introducer and needle are percutaneously inserted into the epidural space at an angle.

14. A method as defined in claim 13 wherein withdrawal of the needle from the central lumen of the introducer shaft causes the distal end of the shaft to be oriented substantially along the axis of the epidural space.

* * * * *